United States Patent
Leblond et al.

(10) Patent No.: US 11,796,475 B2
(45) Date of Patent: Oct. 24, 2023

(54) METHODS FOR PERFORMING A RAMAN SPECTROSCOPY MEASUREMENT ON A SAMPLE AND RAMAN SPECTROSCOPY SYSTEMS

(71) Applicant: Polyvalor, Limited Partnership, Montreal (CA)

(72) Inventors: Frederic Leblond, Terrebonne (CA); Francois Daoust, Pointe-Claire (CA); Sandryne David, Montreal (CA)

(*) Notice: Subject to any disclaimer, the term of this patent is extended or adjusted under 35 U.S.C. 154(b) by 43 days.

(21) Appl. No.: 17/286,304

(22) PCT Filed: Oct. 15, 2019

(86) PCT No.: PCT/CA2019/051458
§ 371 (c)(1),
(2) Date: Apr. 16, 2021

(87) PCT Pub. No.: WO2020/077445
PCT Pub. Date: Apr. 23, 2020

(65) Prior Publication Data
US 2021/0381983 A1   Dec. 9, 2021

Related U.S. Application Data

(60) Provisional application No. 62/746,306, filed on Oct. 16, 2018.

(51) Int. Cl.
*G01J 3/44* (2006.01)
*G01N 21/65* (2006.01)
*A61B 5/00* (2006.01)

(52) U.S. Cl.
CPC ............ *G01N 21/65* (2013.01); *A61B 5/0075* (2013.01)

(58) Field of Classification Search
CPC .. G01N 21/65; G01N 21/314; G01N 21/3151; A61B 5/0075; G01J 3/44; G01J 3/0218; G01J 3/10; G01J 3/32; G01J 3/323
See application file for complete search history.

(56) References Cited

U.S. PATENT DOCUMENTS

| | | | |
|---|---|---|---|
| 10,663,404 B1* | 5/2020 | Babnick | G01J 3/443 |
| 11,119,044 B2* | 9/2021 | Babin | G01M 3/18 |
| 2019/0064072 A1* | 2/2019 | Kim | G01J 3/0216 |

* cited by examiner

Primary Examiner — Uzma Alam
Assistant Examiner — Jonathon Cook
(74) Attorney, Agent, or Firm — JD Patent & Trademark Ltd.; Julian D. Forman

(57) ABSTRACT

There is described a method for performing a Raman spectroscopy measurement on a sample. The method generally has sequentially illuminating an area of said sample with first and second excitation signals, said first excitation signal being slightly spectrally spaced-apart from said second excitation signal, resulting in said area sequentially emitting first and second emission signals; upon receiving said first emission signal, measuring a first intensity value being indicative of optical intensity of said first emission signal within at least a detection band; upon receiving said second emission signal, measuring a second intensity value being indicative of optical intensity of said second emission signal within said detection band; and performing said Raman spectroscopy measurement by comparing said first intensity value to said second intensity value.

1 Claim, 11 Drawing Sheets

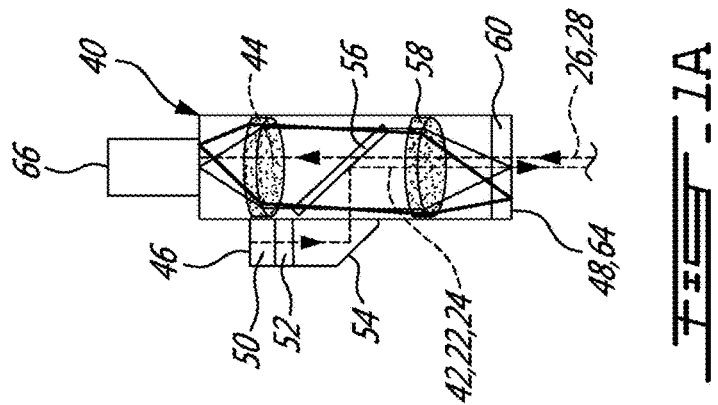
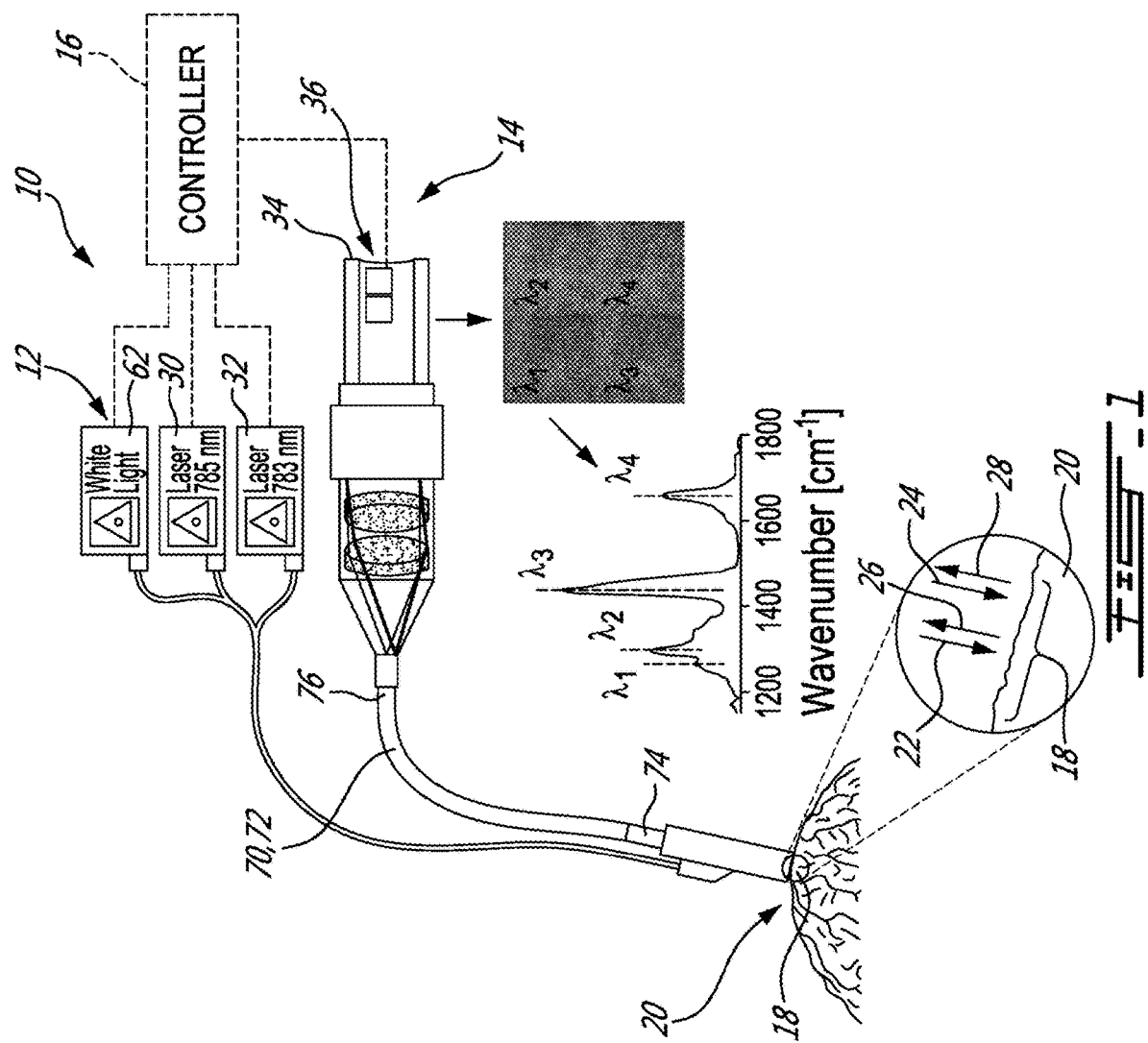

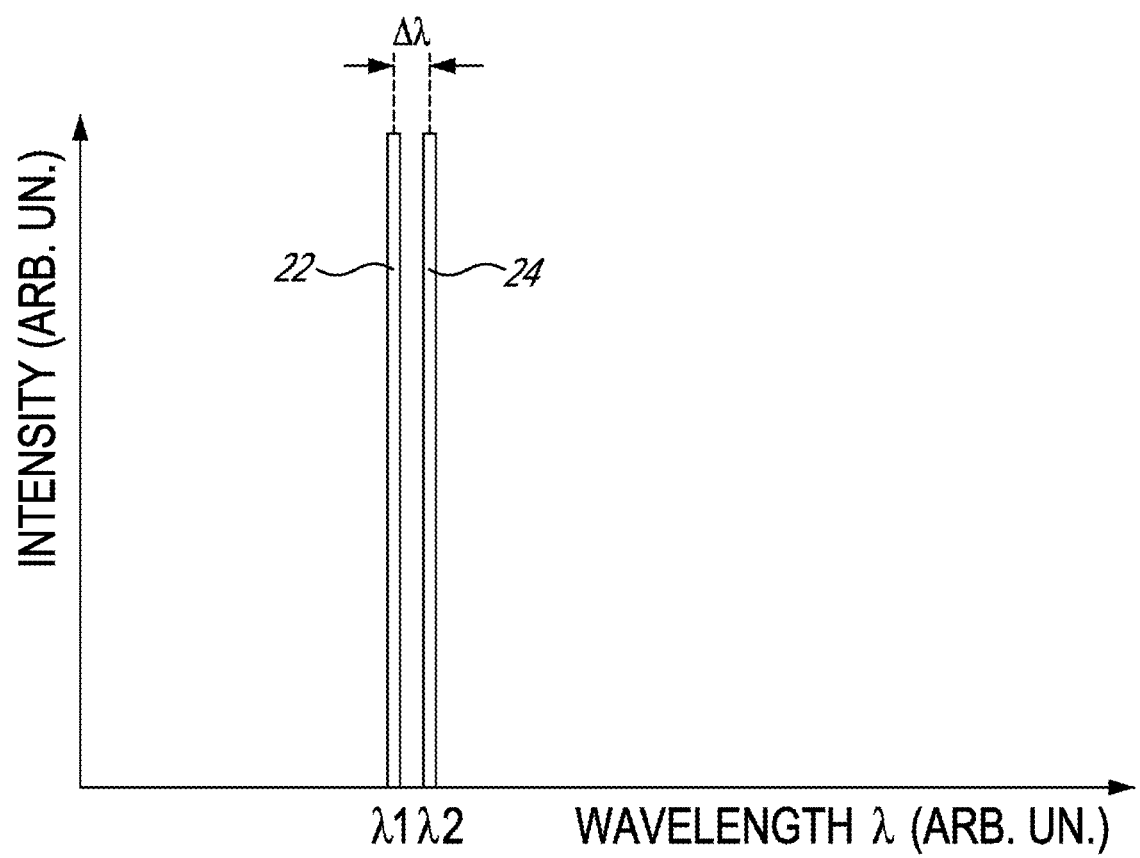

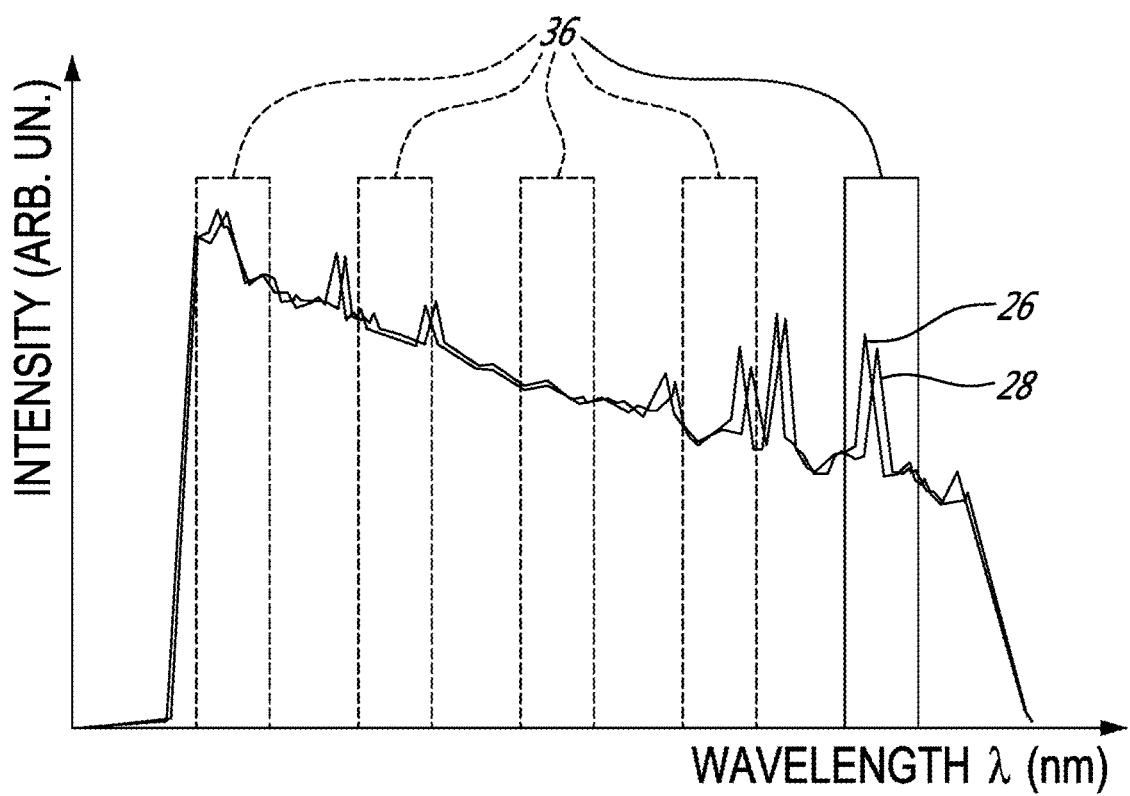

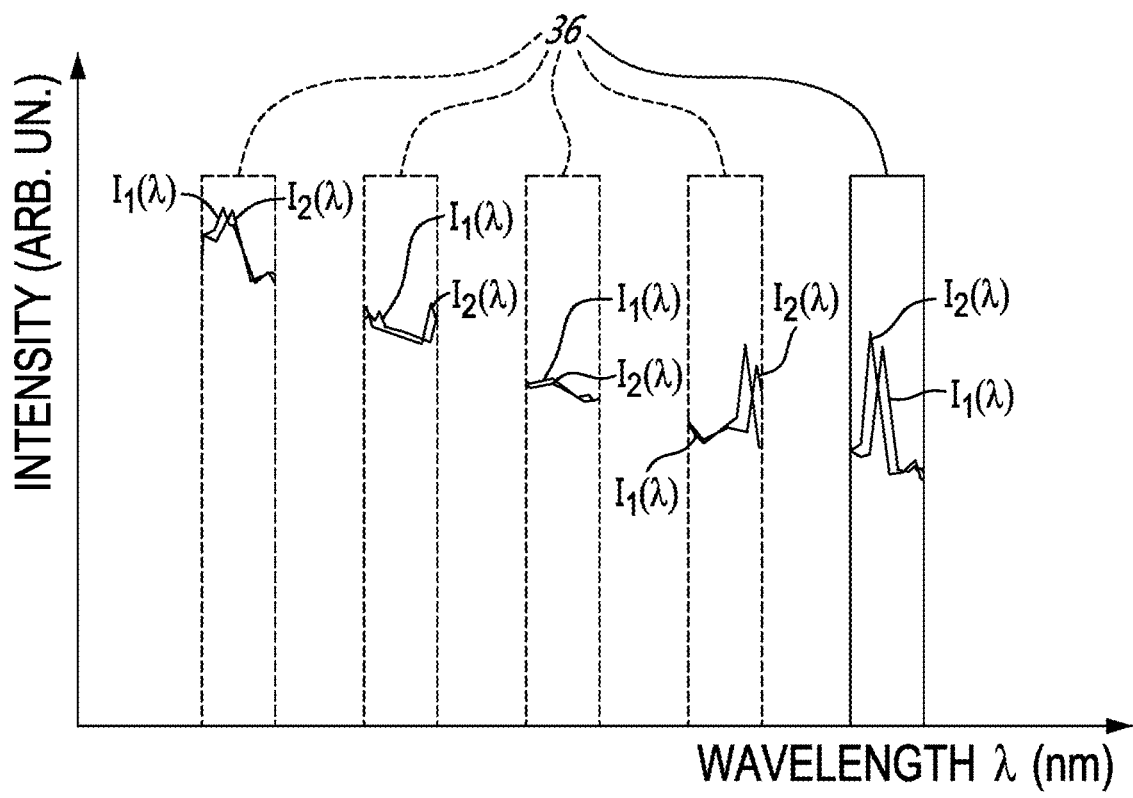
FIG_4

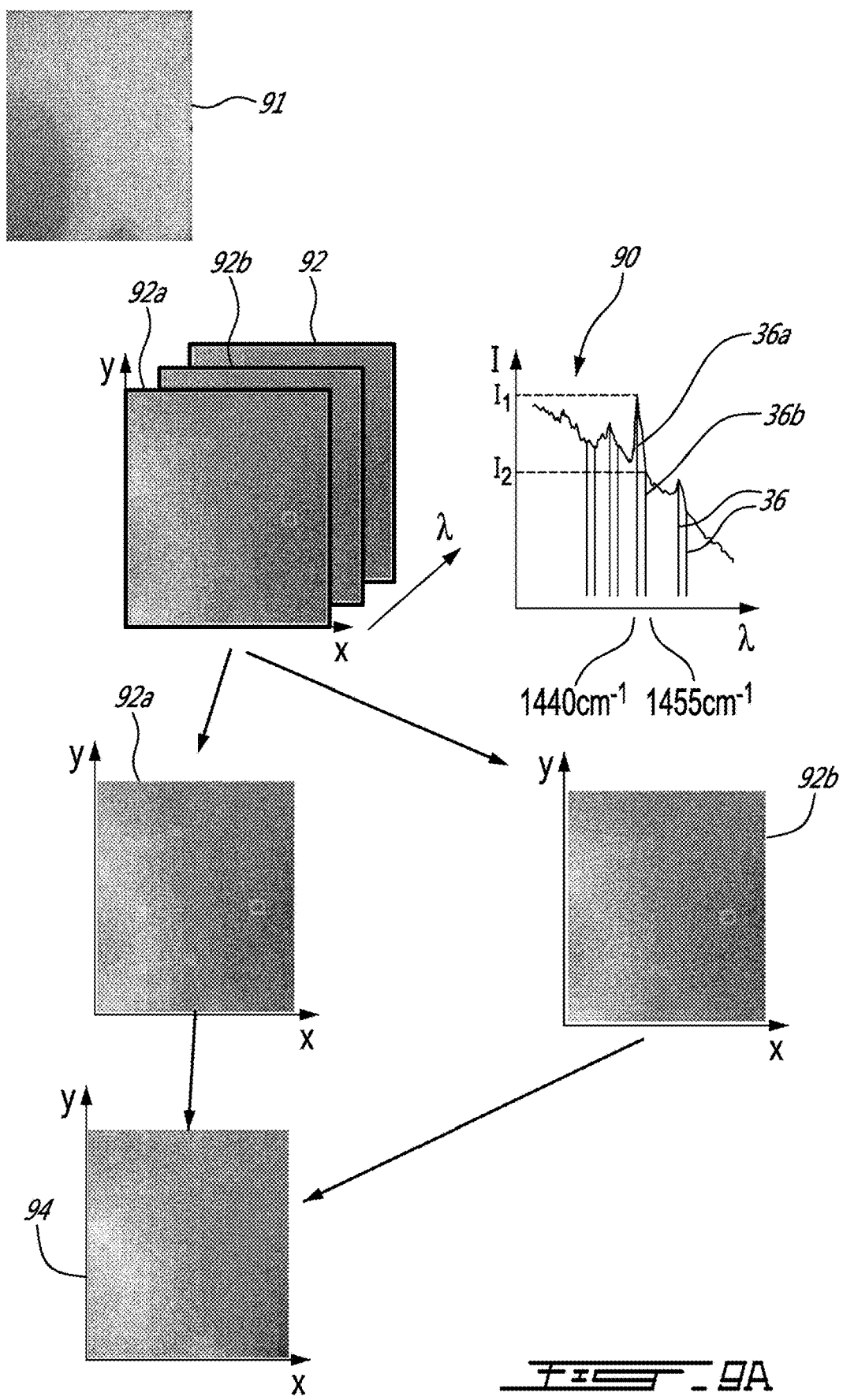

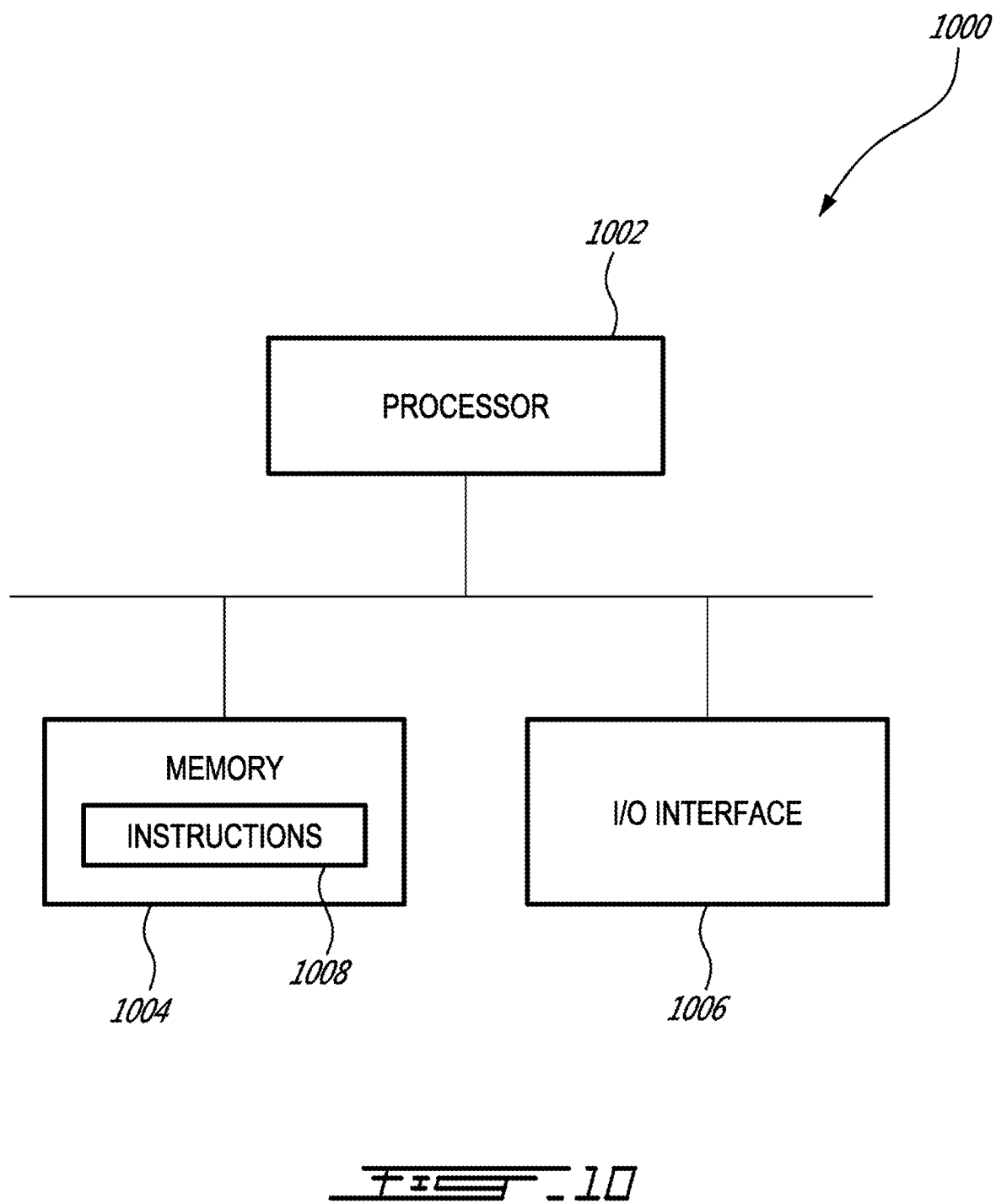

METHODS FOR PERFORMING A RAMAN SPECTROSCOPY MEASUREMENT ON A SAMPLE AND RAMAN SPECTROSCOPY SYSTEMS

REFERENCE TO RELATED APPLICATIONS

This is a U.S. National Stage of International Application PCT/CA2019/051458, filed Oct. 15, 2019, which claims the benefit of priority of U.S. Provisional Application 62/746,306, filed Oct. 16, 2018.

FIELD

The improvements generally relate to the field of Raman spectroscopy, and more particularly relates to intraoperatively performing Raman spectroscopy measurement(s) on a biological sample to guide a surgery.

BACKGROUND

Raman spectroscopy is a spectroscopic technique which can be used to characterize atoms or molecules of a sample. In this technique, the sample is illuminated with an excitation beam, generally comprising monochromatic photons, which excites vibrational, rotational, and/or other low-frequency modes of the atoms or molecules of the sample in a manner which causes them to scatter photons having a different energy level than those of the incident monochromatic photons. The shift(s) in the energy level between the incident photons and the scattered photos gives signature information which can be used to characterize the atoms or molecules of the sample.

It is known that Raman spectroscopy can be used in various fields such as oncology to determine whether a sample contains healthy cells or cancerous cells, based on the respective signature information of such cells. In these fields, optical probes can be used to interrogate a point of the sample, and collect the Raman signal therefrom to determine whether, at that point, the sample contains healthy cells or cancerous cells, a technique often referred to as "single-point Raman spectroscopy". To obtain information concerning an area of the sample, the optical probe is manipulated to interrogate, sequentially, many points of the area of the sample.

Although existing optical probes for Raman spectroscopy are satisfactory to a certain degree, there remains room for improvement.

SUMMARY

According to one aspect, there is described a method and system for imaging an area of a sample using Raman spectroscopy. The method and system involve sequentially illuminating the area of the sample with two excitation signals which are only slightly spectrally spaced-apart from one another. When so-illuminated, both the two excitation signals can cause the sample to emit a respective emission signal comprising a Raman component and a noise component. Generally, the Raman component has a stronger dependence on the spectral content of the excitation signal than the noise component. Accordingly, the Raman component may be stronger or weaker depending on which one of the first and second excitation signals is used as their respective spectral contents differ. In contrast, the noise component may remain relatively similar upon excitation using either one of the first and second excitation signals. Raman scattering is an example of such a Raman component whereas auto-fluorescence is an example of such a noise component.

Accordingly, by measuring the emission signals in a plurality of spaced-apart detection bands, and by comparing the measurements of the emission signals, the method and system can discriminate the noise components from the findings, in order to focus on the Raman components, which when compared to one another, can enhance their relative importance and facilitate the Raman spectroscopy measurements.

It was found that measuring the emission signals only in such spaced-apart detection bands, in contrast with taking full spectrum measurements, can accelerate the rate at which Raman spectroscopy measurements could be made, which is convenient in situations where the method and system are to be used intraoperatively to determine whether the area of the sample comprise healthy or unhealthy biological tissue (e.g., cancerous tissue) during a surgery. In some embodiments, the method and system can involve the use of a bundle of optical fibers in the illumination/excitation of the sample, in the collection of Raman signal from the sample, or both. It is envisaged that in some embodiments, the intensity values of the first and second emission signals can be measured within only one detection band.

In accordance with a first aspect of the present disclosure, there is provided a method for performing a Raman spectroscopy measurement on a sample, the method comprising: sequentially illuminating an area of said sample with first and second excitation signals, said first excitation signal being slightly spectrally spaced-apart from said second excitation signal, resulting in said area sequentially emitting first and second emission signals; upon receiving said first emission signal, measuring a first intensity value being indicative of optical intensity of said first emission signal within at least a detection band; upon receiving said second emission signal, measuring a second intensity value being indicative of optical intensity of said second emission signal within said detection band; and performing said Raman spectroscopy measurement by comparing said first intensity value to said second intensity value.

Further in accordance with the first aspect of the present disclosure, said measuring a first intensity value can for example comprise measuring, for a plurality of spectrally spaced-apart detection bands, corresponding ones of a plurality of first intensity values being indicative of optical intensity of said first emission signal within said spectrally spaced-apart detection bands, and wherein said measuring a second intensity value comprises measuring, for said plurality of spectrally spaced-apart detection bands, corresponding ones of a plurality of second intensity values being indicative of optical intensity of said second emission signal within said spectrally spaced-apart detection bands.

Still further in accordance with the first aspect of the present disclosure, the plurality of spectrally spaced-apart detection bands can for example have between 1 and 2000 spectrally spaced-apart detection bands, preferably between 1 and 200 spectrally spaced-apart detection bands and most preferably between 1 and 20 spectrally spaced-apart detection bands.

Still further in accordance with the first aspect of the present disclosure, the plurality of spectrally spaced-apart detection bands can for example be evenly spaced-apart from one another.

Still further in accordance with the first aspect of the present disclosure, at least one of said spectrally spaced-apart detection bands can have for example a spectral width between about 0.1 nm and about 10 nm, preferably between about 0.1 nm and about 5 nm, most preferably between about 0.2 nm and 2 nm.

Still further in accordance with the first aspect of the present disclosure, said first and second excitation signals can for example be spectrally spaced-apart by a spectral spacing of between 0.1 nm to 5 nm and most preferably between 0.3 nm and 2 nm.

Still further in accordance with the first aspect of the present disclosure, the first excitation signal can have for example optical power at 785 nm, and the second excitation signal can have for example optical power at 783 nm.

Still further in accordance with the first aspect of the present disclosure, said comparing can for example include subtracting said first intensity value from said second intensity value.

Still further in accordance with the first aspect of the present disclosure, the method can for example include a step of determining whether a region of said area of said sample is unhealthy.

Still further in accordance with the first aspect of the present disclosure, said determining can for example include delimiting said unhealthy tissue from said healthy tissue.

Still further in accordance with the first aspect of the present disclosure, the method can for example include a step of determining whether a region of said area of said sample contains two or more molecular constituents.

Still further in accordance with the first aspect of the present disclosure, said sequentially illuminating can for example comprise sequentially illuminating an area of said sample with first, second and third excitation signals, said first, second and third excitation signals being slightly spectrally spaced-apart from one another, resulting in said area sequentially emitting first, second and third emission signals, the method further comprising measuring a third intensity value indicative of optical intensity of said third emission signal within said detection band, said comparing said first intensity value to said second intensity value comprising estimating a fourth intensity value at said detection band based on the first and second intensity values, said performing comprising comparing said fourth intensity value to the third intensity value.

In accordance with a second aspect of the present disclosure, there is provided a Raman spectroscopy system comprising: an illumination assembly sequentially illuminating an area of a sample with first and second excitation signals, said first excitation signal being slightly spectrally spaced-apart from said second excitation signal, resulting in said area sequentially emitting first and second emission signals; a receiver assembly receiving said first and second emission signals, the receiving assembly having at least a detector measuring a first intensity value being indicative of optical intensity of said first emission signal within at least a detection band and measuring a second intensity value being indicative of optical intensity of said second emission signal within said detection band; and a controller being communicatively coupled to said receiver assembly, said controller having a processor and a memory having stored thereon instructions that when executed by said processor performs the step of comparing said first intensity value to said second intensity value.

Further in accordance with the second aspect of the present disclosure, the receiver assembly can for example have a plurality of detectors measuring, for a plurality of spectrally spaced-apart detection bands, corresponding ones of a plurality of first intensity values being indicative of optical intensity of said first emission signal within said spectrally spaced-apart detection bands, and measuring, for said plurality of spectrally spaced-apart detection bands, corresponding ones of a plurality of second intensity values being indicative of optical intensity of said second emission signal within said spectrally spaced-apart detection bands.

Still further in accordance with the second aspect of the present disclosure, the plurality of spectrally spaced-apart detection bands of said receiver assembly can for example have between 1 and 2000 spectrally spaced-apart detection bands, preferably between 1 and 200 spectrally spaced-apart detection bands and most preferably between 1 and 20 spectrally spaced-apart detection bands.

Still further in accordance with the second aspect of the present disclosure, at least one of said spectrally spaced-apart detection bands can for example have a spectral width between about 0.1 nm and about 10 nm, preferably between about 0.1 nm and about 5 nm, most preferably between about 0.2 nm and 2 nm.

Still further in accordance with the second aspect of the present disclosure, said first and second excitation signals can for example be spectrally spaced-apart by a spectral spacing of between 0.1 nm to 5 nm and most preferably between 0.3 nm and 2 nm.

Still further in accordance with the second aspect of the present disclosure, said illumination assembly can for example have a first excitation signal source configured for emitting said first excitation signal at 785 nm, and a second excitation signal source configured for emitting said second excitation signal at 783 nm.

Still further in accordance with the second aspect of the present disclosure, said receiver assembly can have for example a bundle of optical fibres.

Still further in accordance with the second aspect of the present disclosure, said optical fibers of said bundle can for example extend between first ends and second ends, said first ends and said second ends of said plurality of optical fibers being arranged in a respective one of two two-dimensional arrays.

Still further in accordance with the second aspect of the present disclosure, said two two-dimensional arrays can for example maintain relative positions of said optical fibers to one another from said first ends to said second ends in a manner that said received first and second emission signals are propagated along the bundle of optical fibers while maintaining said relative positions from said first ends towards said second ends.

It is intended that the use of the term "slightly" in the passage "the first excitation signal being slightly spectrally spaced-apart from the second excitation signal" or any other equivalent passage is to be interpreted broadly so as to encompass any situation where the spectral shift between the first and second excitation signals is sufficiently small so that noise components of the first and second emission signals remain relatively similar to one another.

In accordance with a third aspect of the present disclosure, there is provided a method for performing a Raman spectroscopy measurement on a sample, the method comprising: illuminating an area of said sample with an excitation signal, resulting in said area emitting an emission signal; upon receiving said emission signal, measuring a first intensity value being indicative of optical intensity of said emission signal within a first detection band and measuring a second intensity value being indicative of optical intensity of said emission signal within a second detection band, said first detection band being spectrally spaced-apart from said second detection band; and performing said Raman spectroscopy measurement by comparing said first intensity value to said second intensity value.

Further in accordance with the third aspect of the present disclosure, said measuring can for example comprise measuring a plurality of intensity values being indicative of optical intensity of said emission signal within corresponding ones of a plurality of spectrally spaced-apart detection bands.

Still further in accordance with the third aspect of the present disclosure, the plurality of spectrally spaced-apart detection bands can for example have between 1 and 2000 spectrally spaced-apart detection bands, preferably between 1 and 200 spectrally spaced-apart detection bands and most preferably between 1 and 20 spectrally spaced-apart detection bands.

Still further in accordance with the third aspect of the present disclosure, the plurality of spectrally spaced-apart detection bands can for example be evenly spaced-apart from one another.

Still further in accordance with the third aspect of the present disclosure said measuring can for example comprises measuring a third intensity value indicative of optical intensity of said emission signal within a third detection band, said third detection band being spectrally spaced-apart from said first and second detection bands, said comparing said first intensity value to said second intensity value comprising estimating a fourth intensity value at said third detection band based on the first and second intensity values, said performing comprising comparing said fourth intensity value to the third intensity value.

Still further in accordance with the third aspect of the present disclosure said estimating can for example comprise performing a linear regression between the first and second intensity values, and finding an intensity value at the third detection band based on said linear regression.

Still further in accordance with the third aspect of the present disclosure, at least one of said first and second detection bands can for example have a spectral width between about 0.1 nm and about 10 nm, preferably between about 0.1 nm and about 5 nm, most preferably between about 0.2 nm and 2 nm.

Still further in accordance with the third aspect of the present disclosure, said first and second detection bands can for example be spectrally spaced-apart by a spectral spacing of between 0.1 nm to 5 nm and most preferably between 0.3 nm and 2 nm.

Still further in accordance with the third aspect of the present disclosure, the excitation signal can for example have optical power at 785 nm.

Still further in accordance with the third aspect of the present disclosure, said comparing can for example include subtracting said first intensity value from said second intensity value.

Still further in accordance with the third aspect of the present disclosure, the method can for example further comprise determining whether a region of said area of said sample is unhealthy.

Still further in accordance with the third aspect of the present disclosure, said determining can for example include delimiting said unhealthy tissue from said healthy tissue.

Still further in accordance with the third aspect of the present disclosure, the method can for example further comprise determining whether a region of said area of said sample contains two or more molecular constituents.

In accordance with a fourth aspect of the present disclosure, there is provided a Raman spectroscopy system comprising: an illumination assembly illuminating an area of a sample with an excitation signal, resulting in said area emitting an emission signal; a receiver assembly receiving said emission signal, the receiving assembly having at least a detector measuring a first intensity value being indicative of optical intensity of said emission signal within a first detection band and measuring a second intensity value being indicative of optical intensity of said emission signal within a second detection band, said first detection band being spectrally spaced-apart from said second detection band; and a controller being communicatively coupled to said receiver assembly, said controller having a processor and a memory having stored thereon instructions that when executed by said processor performs the step of comparing said first intensity value to said second intensity value.

Further in accordance with the fourth aspect of the present disclosure, said receiver assembly can for example measure a plurality of intensity values being indicative of optical intensity of said emission signal within corresponding ones of a plurality of spectrally spaced-apart detection bands.

Still further in accordance with the fourth aspect of the present disclosure, the plurality of spectrally spaced-apart detection bands can for example have between 1 and 2000 spectrally spaced-apart detection bands, preferably between 1 and 200 spectrally spaced-apart detection bands and most preferably between 1 and 20 spectrally spaced-apart detection bands.

Still further in accordance with the fourth aspect of the present disclosure, the plurality of spectrally spaced-apart detection bands can for example have evenly spaced-apart from one another.

Still further in accordance with the fourth aspect of the present disclosure, said measuring can for example further comprise measuring a third intensity value indicative of optical intensity of said emission signal within a third detection band, said third detection band being spectrally spaced-apart from said first and second detection bands, said comparing said first intensity to said second intensity values comprising estimating a fourth intensity value indicative of optical power of said emission signal at said third detection band, said performing comprising comparing said fourth intensity value to the third intensity value.

Still further in accordance with the fourth aspect of the present disclosure, said estimating can for example comprise performing a linear regression between the first and second intensity values, and finding an intensity value at the third detection band based on said linear regression.

Still further in accordance with the fourth aspect of the present disclosure, said receiver assembly can for example have a bundle of optical fibres.

Many further features and combinations thereof concerning the present improvements will appear to those skilled in the art following a reading of the instant disclosure.

DESCRIPTION OF THE FIGURES

In the figures,

FIG. 1 is a schematic view of an example of a system for performing a Raman spectroscopy measurement, in accordance with an embodiment;

FIG. 1A is a sectional and enlarged view of an example of a probe of the system of FIG. 1, in accordance with an embodiment;

FIG. 2 is a graph showing intensity as function of wavelength, with first and second excitation signals being spectrally spaced-apart from one another, in accordance with an embodiment;

FIG. 3 is a graph showing intensity as function of wavelength, with the entire spectral content of first and second emission signals, in accordance with an embodiment;

FIG. 4 is a graph showing intensity as function of wavelength, with first and second emission signals, as received in spectrally-spaced apart detection bands of the system of FIG. 1, in accordance with an embodiment;

FIG. 9A is a flow chart of an example of a method of performing a Raman spectroscopy measurement, involving a single excitation signal and a plurality of detection bands, in accordance with an embodiment;

FIG. 10 is a schematic view of an example of a computing device of the system of FIG. 1, in accordance with an embodiment.

DETAILED DESCRIPTION

Figure 5:
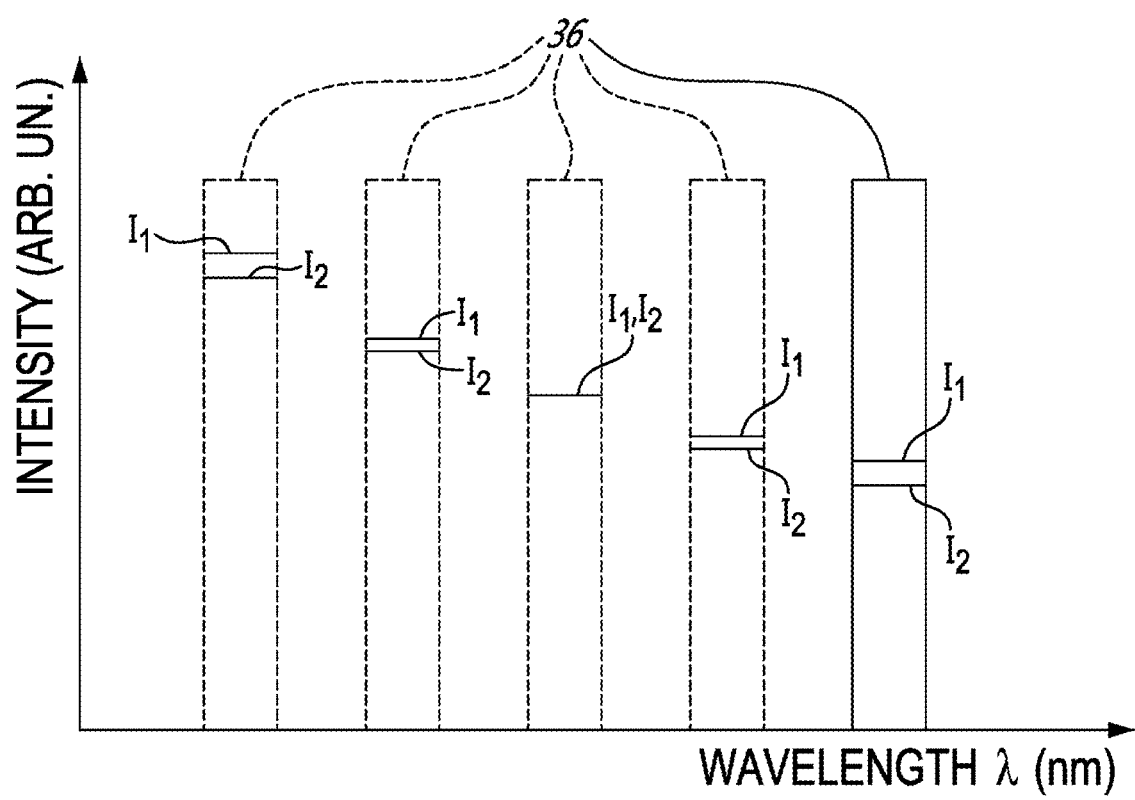
FIG. 5 is a graph showing intensity as function of wavelength, with intensity values of the first and second emission signals being measured in each of the spectrally-spaced apart detection bands of the system of FIG. 1, in accordance with an embodiment.

FIG. 1 is an example of a Raman spectroscopy system 10, in accordance with an embodiment. As depicted in this example, the Raman spectroscopy system 10 has an illumination assembly 12, a receiver assembly 14 and a controller 16.

As shown, the illumination assembly 12 is configured for sequentially illuminating an area 18 of a sample 20 with first and second excitation signals 22 and 24. In other words, the area 18 of the sample 20 is illuminated first with the first excitation signal 22 and then with the second excitation signal 24, or vice versa. As can be understood, illuminating the area 18 of the sample 20 in such a manner will result in the area 18 sequentially emitting first and second emission signals 26 and 28 in response to the illumination with the first and second excitation signals 22 and 24, respectively.

As shown in FIG. 2, the first excitation signal 22 is spectrally spaced-apart from the second excitation signal 24. In some embodiments, the first and second excitation signals 22 and 24 are spectrally spaced-apart by a spectral spacing between 0.1 nm to 5 nm depending on the sample and its Raman bands and most preferably between 0.3 nm and 2 nm for biological samples.

Referring back to FIG. 1, the illumination assembly 12 has a first excitation signal source 30 configured for emitting said first excitation signal 22 within the 785 nm-band, and a second excitation signal source 32 configured for emitting said second excitation signal 24 within the 783 nm-band. Accordingly, in this specific example, the spectral spacing between the first and second excitation signals 22 and 24 is about 2 nm.

However, in other embodiments, the first and second excitation signals 22 and 24 can be emitted using a single optical source which is configured for emitting the first and second excitation signals 22 and 24 sequentially such as with tunable optical sources.

As shown, the receiver assembly 14 is configured for receiving the first and second emission signals 26 and 28 upon their respective emission, and for directing optical power of the first and second emission signals 26 and 28 within a plurality of spaced-apart detection bands 36 to corresponding ones of a plurality of detectors 34. In this example, the detectors 34 are part of a multispectral camera 36. However, in some other embodiments, the detectors 34 can be part of an hyperspectral camera or be provided as a standalone array of detectors.

FIG. 3 shows an example of the spectral content of the first and second emission signals 26 and 28 over which are overlaid spaced-apart detection bands 36. FIG. 4 shows an example of the spectral contents $I_1(\lambda)$ and $I_2(\lambda)$ of the first and second emission signals 26 and 28 which are being measured within the spaced-apart detection bands 36 by the detectors 34.

It is emphasized in this example that the detectors 34 are configured for measuring corresponding ones of first intensity values $I_1$ which are indicative of optical intensity within each of the spaced-apart detection bands 36 in the first emission signal 26. Similarly, the detectors 34 are configured for measuring corresponding ones of second intensity values $I_2$ which are indicative of optical intensity within each of the spaced-apart detection bands 36 in the second emission signal 28. FIG. 5 shows an example of the first and second intensity values $I_1$ and $I_2$ as measured by the detectors 34 in each of the spaced-apart detection bands 36.

As such, by comparing, the first intensity value $I_1$ to the second intensity value $I_2$ for each of the spaced-apart detection bands 36, noise components of the first and second emission signals 26 and 28 can be attenuated, and even canceled, with one another while enhancing Raman components of the first and second emission signals 26 and 28.

Figure 6:
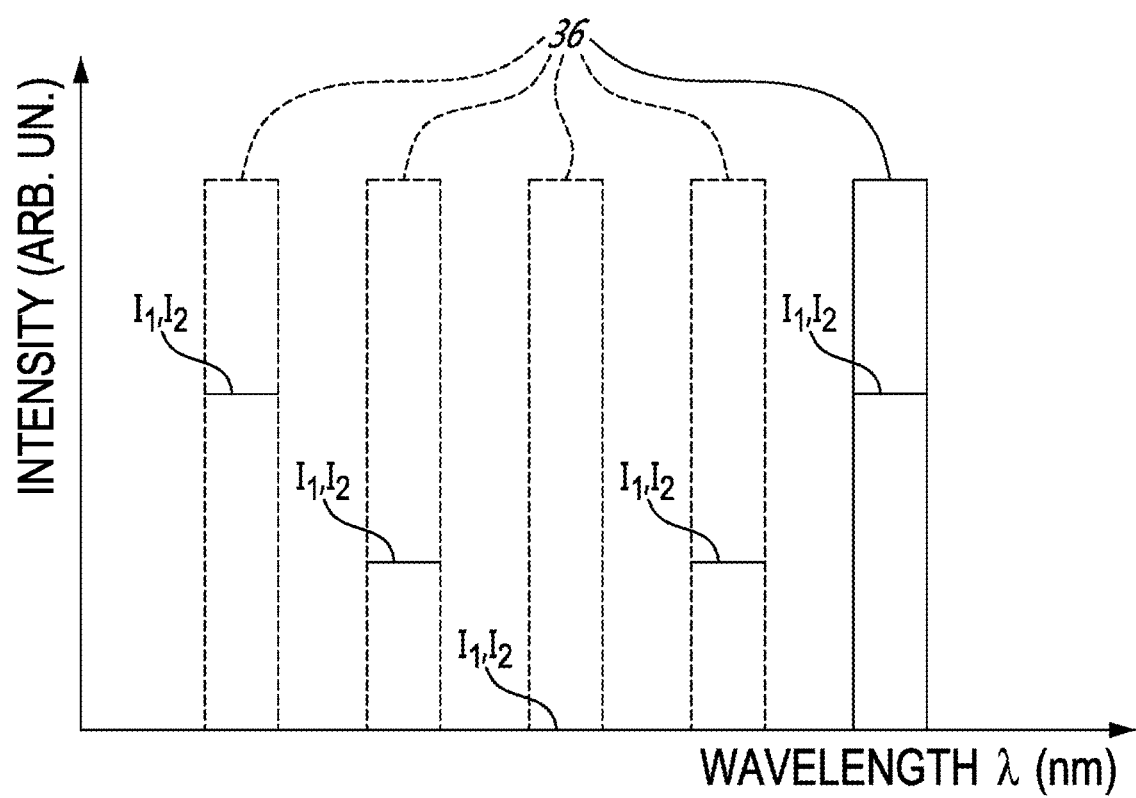
FIG. 6 is a graph showing intensity as function of wavelength. with intensity values of the first and second emission signals being compared to one another in each of the spectrally-spaced apart detection bands of the system of FIG. 1, in accordance with an embodiment.

Accordingly, the system 10 can allow performing a Raman spectroscopy measurement based on this comparison. In some embodiments, the comparison process can include subtractions of the first intensity values $I_1$ from the second intensity values $I_2$, as schematically illustrated in FIG. 6.

It is envisaged that the way the first and second intensity values $I_1$ and $I_2$ are measured within each spaced-apart detection bands 36 can differ from an embodiment to another. For instance, in this embodiment, the first intensity values $I_1$ correspond to a maximal value of the first emission signal 26 in a corresponding one of the spaced-apart detection bands 36 whereas the second intensity values $I_2$ correspond to a minimal value of the second emission signal 28 in the corresponding one of the spaced-apart detection bands 36. In some other embodiments, the first intensity values $I_1$ correspond to the intensity integrated over a corresponding one of the spaced-apart detection bands 36 where the second intensity value $I_2$ correspond to the intensity integrated over the corresponding one of the spaced-apart detection bands 36.

Depending on the embodiment, the spaced-apart detection bands 36 of the receiver assembly 14 has between 1 and 2000 spaced-apart detection bands 36, preferably between 1 and 200 spaced-apart detection bands 36 and most preferably between 1 and 20 spaced-apart detection bands 36. It is noted that the speed at which Raman spectroscopy measurements can be performed is generally inversely proportional with the number of spaced-apart detection bands 36. In other words, the lesser the number of spaced-apart detection bands 36 is, the quicker Raman spectroscopy measurements can be performed.

In some embodiments, the spaced-apart detection bands 36 are evenly spaced-apart whereas the spaced-apart detection bands 36 are unevenly spaced-apart in some other embodiments. For instance, the spaced-apart detection bands can be concentrated over a given spectral region where more Raman scattering is expected from a given type of sample.

It is intended that in some embodiments, each spaced-apart detection band 36 has a spectral width between about 0.1 nm and about 10 nm, preferably between about 0.1 nm and about 5 nm, most preferably between about 0.2 nm and 2 nm. However, in some other embodiments, the spectral widths of the spaced-apart detection bands 36 can differ from one another. For instance, in some embodiments, the receiver assembly 14 can include one or more filter wheel(s) having laser line filter(s) incorporated thereto to select the spectral width of the integrated signal as well as that of the detection band.

Measuring the first and second intensity values in more than one of the spectrally spaced-apart detection bands 36 can be omitted in some embodiments. For instance, the first and second intensity values can be measured in only one of the spectrally spaced-apart detection bands 36. For example, in some embodiments, the first and second intensity values are measured only in the right-hand one of the detection bands 36, as shown in solid lines in FIGS. 3-6.

Referring back to FIG. 1, the controller 16 in this example is communicatively coupled (e.g., wiredly, wirelessly or both) to the detectors 34. Accordingly, the controller 16 receive the first and second intensity values $I_1$ and $I_2$ from the detectors 34 and perform the comparison (e.g., subtraction $I_1 - I_2$), and other additional yet optional processing steps, depending on the application.

FIG. 1A shows an example of a probe 40 of the system 10 of FIG. 1. As depicted, the probe 40 encloses both an excitation path 42 and an emission path 44. More specifically, the prove body 40 has an excitation input 46 where the first and second excitation signals 22 and 24 are received and transmitted at an excitation output 48 directed toward the area of the sample. In this specific example, the first and second excitation signals 22 and 24 are collimated using a collimation lens 50, filtered using a laserline filter 52, and directed toward the excitation output 48 using a mirror 54 and a dichroic beam splitter 56 prior to being focusing, using a focusing lens 58, through an optical window 60 towards the area of the sample. In this specific embodiment, the illumination assembly 14 includes a white light source 62 which is coupled along the excitation path 42 in order to illuminate the area of the sample, which can be convenient during a surgery.

Still in this example, the excitation output 48 of the probe 40 acts also as an emission input 64 where the first and second emission signals 26 and 28 are picked up using the focusing lens 58 which collimates the first and second emission signals 26 and 28 in direction of the dichroic notch filter 56, and ultimately towards an emission output 66 of the probe 40.

Figure 7:
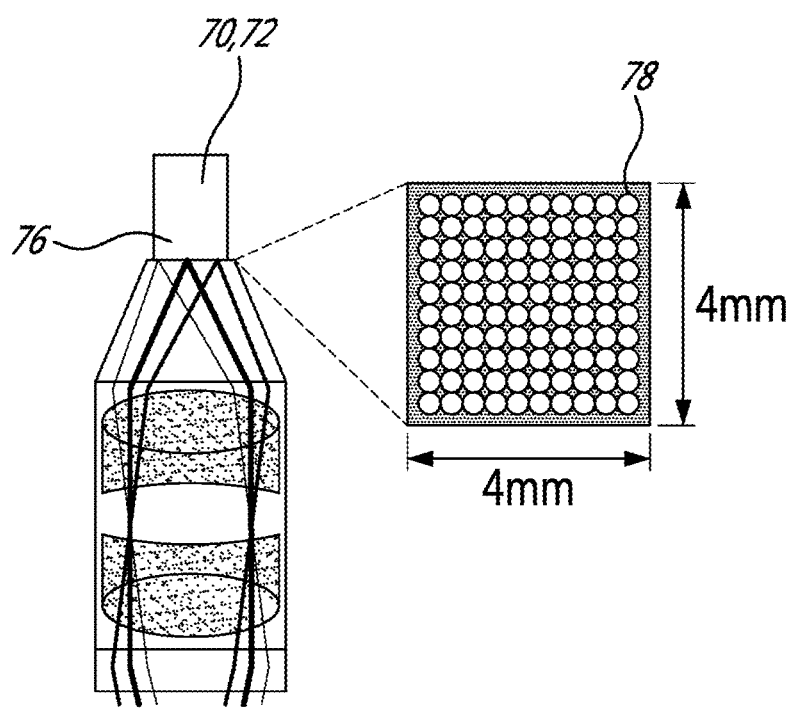
FIG. 7 is a schematic view of another example of a probe of the system of FIG. 1, in accordance with an embodiment.

In this specific embodiment, the emission output 66 of the probe 40 is optically coupled to the detectors 34 via a plurality of optical fibres 70, i.e., a bundle 72 of optical fibres 70. More specifically, the optical fibers 70 of the bundle 72 extend between first ends 74 and second ends 76, where the first ends 74 and the second ends 76 of the optical fibers 70 are arranged in a respective one of two two-dimensional arrays 78, as best seen in FIG. 7. In this way, the two two-dimensional arrays 78 maintain relative positions of the optical fibers 70 to one another from the first ends 74 to the second ends 76 in a manner that the received first and second emission signals 26 and 28 are propagated along the bundle 72 of optical fibers 70 while maintaining the relative positions from the first ends 74 towards the second ends 76. In some embodiments, such a bundle 72 of optical fibres 70 can allow imaging of the area of the sample. In this example, the two-dimensional arrays 78 are in arrays of 400 fibres× 400 fibres, in which both sides of the array measure about 4 mm. An example of such a bundle 72 of optical fibers 70 is described in International Application Serial no. PCT/CA2018/051140, which is hereby incorporated by reference.

Figure 8C:
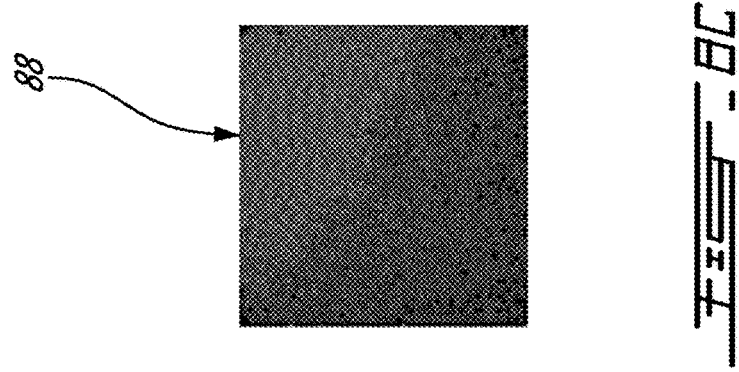
FIG. 8C is a two-dimensional map of the area of the sample of FIG. 8B, with a first region associated to muscular tissue and a second region associated to adipose tissue, obtained using the system of FIG. 1, in accordance with an embodiment.
Figure 8B:
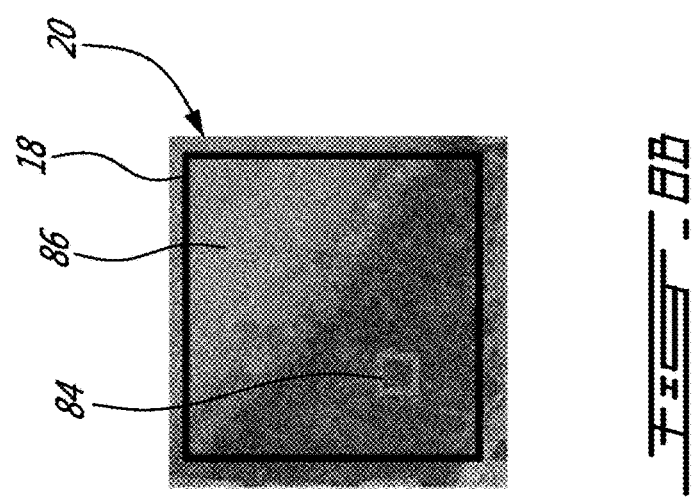
FIG. 8B is an image of an area of a biological sample comprising muscular and adipose tissues, in accordance with an embodiment.
Figure 8A:
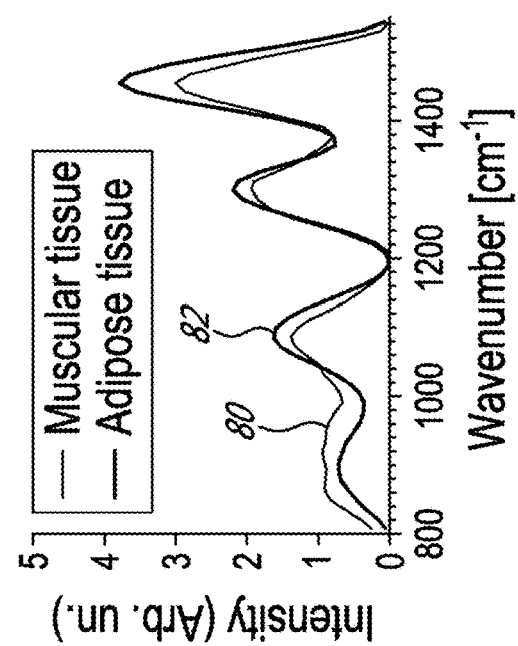
FIG. 8A is a graph showing intensity as function of wavenumber, with Raman components of muscular and adipose tissues, in accordance with an embodiment.

FIG. 8A shows an example of Raman components of emission signals 80 and 82 for muscular and adipose tissue, respectively, as taken with a single-point Raman probe. FIG. 8B shows an area 18 of a sample 20 comprising both muscular and adipose tissue 84 and 86. In this embodiment, the system 10 of FIG. 1 has been used to determine whether a region of the area 18 constitutes muscular tissue 84 or adipose tissue 86, in which case a map 88 delimiting the muscular tissue 84 from the adipose tissue 86 could be produced, as shown in FIG. 8C. The color of each pixel in map 88 is indicative of the difference between the first and second intensities as measured at each point of the area 18 of the sample 20.

FIG. 9A shows a flow chart of an example of a method for performing a Raman spectroscopy measurement on a sample. After having illuminated an area of a sample with an excitation signal, as shown at white light image 91, an emission signal is emitted by the area. Graph 90 shows an exemplary spectrum of the emission signal. As shown, in this example the emission signal is measured so as to provide at least a first intensity value $I_1$ which is indicative of optical intensity of the emission signal within a first detection band 36a. Simultaneously, or sequentially, the emission signal is measured to provide a second intensity value $I_2$ which is indicative of optical intensity of the emission signal within a second detection band 36b. For instance, in this specific embodiment, the first detection band 36a is at 1440 cm$^{-1}$ whereas the second detection band 36b is at 1455 cm$^{-1}$. As depicted, the detection bands 36a and 36b are spectrally spaced-apart from another. In this method, a Raman spectroscopy measurement is performed by comparing the first and second intensity values $I_1$ and $I_2$ to one another.

In some embodiments, other intensity values could also be measured at other detection bands 36. In these embodiments, the Raman spectroscopy measurement could be performed by comparing any two of the first, second, or other intensity values to one another.

As discussed above, the area of a sample can be interrogated spatially so as to measure emission signals from a plurality of coordinates x and y of the sample. Intensity maps 92a, 92b and 92 show intensity values as measured within each one of the detection bands 36a, 36b and 36, respectively, which may result from such a scanning step. For instance, each intensity value of the intensity map 92a is indicative of the intensity of the emission signal measured, within the first detection band 36a, at a corresponding coordinate x and y of the area of the interrogated sample.

Intensity map 94 shows the result of an exemplary comparison between the intensity maps 92a and 92b. In this specific example, as the first detection band 36a is associated to a lipid band peak and the second detection band 36b is associated to a lipid band minimum, the resulting intensity map 94, resulting from subtracting the intensity maps 36a and 36b to one another, can be indicative of the lipid band.

Figure 9B:
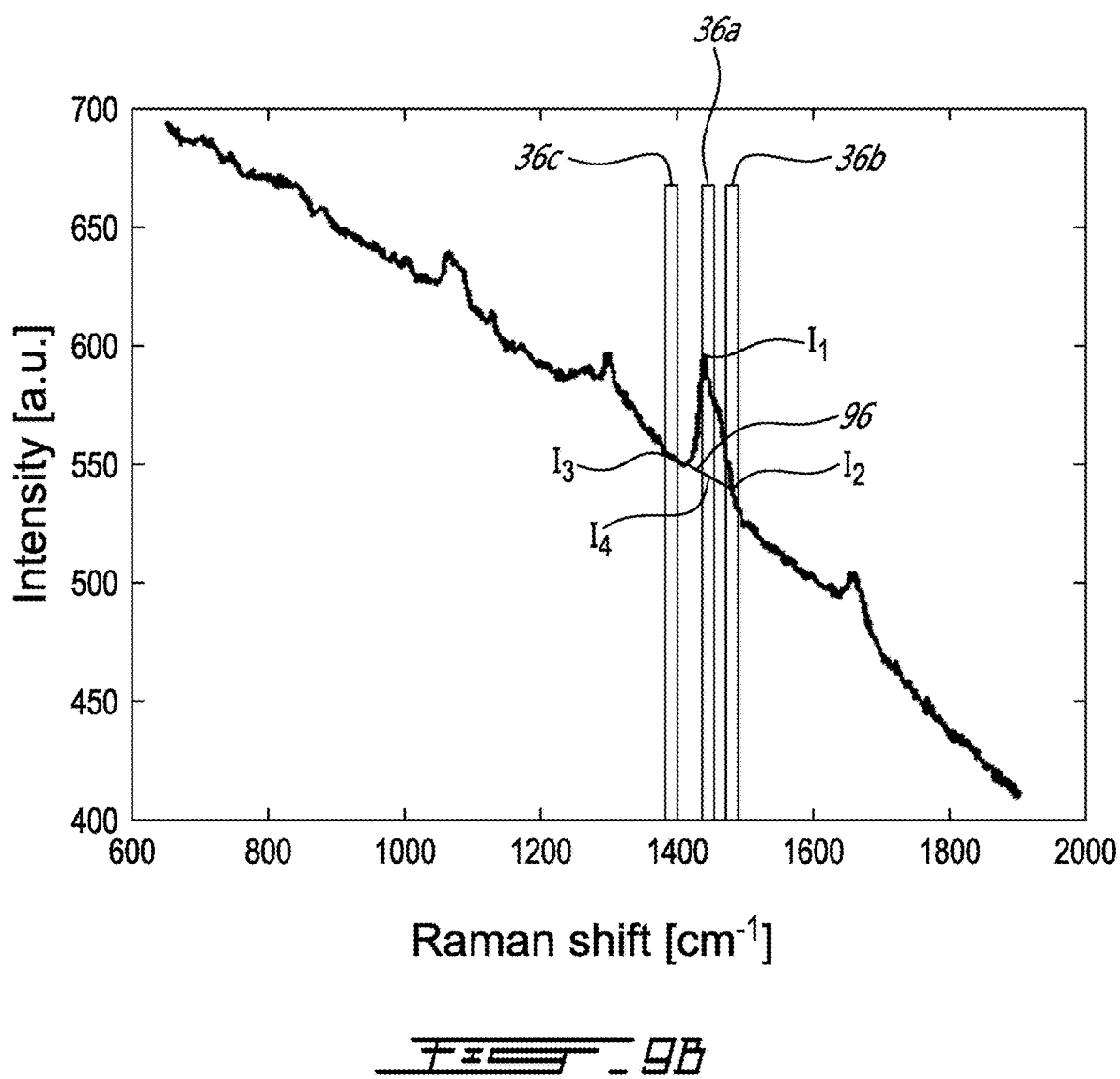
FIG. 9B is a graph of intensity versus Raman shift, showing a linear regression between some of the detection bands of FIG. 9A, in accordance with an embodiment.

FIG. 9B illustrates an example of the method described with reference to FIG. 9A. As shown, first and second intensity values $I_1$ and $I_2$ are measured at first and second detection bands 36a and 36b, respectively. In this specific embodiment, a third intensity value $I_3$ indicative of optical intensity of the emission signal within a third detection band 36c is measured. The Raman spectroscopic measurement is performed by estimating a fourth intensity value $I_4$ indicative of optical power of the emission signal at the first detection band 36a. In this specific embodiment, the estimation can be performed on the basis of a linear regression 96 (e.g., interpolation, extrapolation) using the first and second intensity values $I_1$ and $I_2$ such as to allow the fourth intensity value $I_4$ to be found at the first detection band 36a. Once the fourth intensity value $I_4$ is determined, the Raman spectroscopy measurement can be performed by comparing the first and fourth intensity values $I_1$ and $I_4$ to one another. As can be understood, in this example, the first intensity value $I_1$ is associated to the lipid band peak, the second intensity value $I_2$ is associated to a first lipid band minimum, the third intensity value $I_3$ is associated to a second lipid band minimum, accordingly the fourth intensity value $I_4$ is associated to the lipid band peak minus an average of the first and second lipid band minima.

In the embodiment described with reference to FIG. 9B, only one excitation signal is used to excite the area of the sample, resulting in multiple detection bands each measuring a respective portion of the emission spectrum for comparison purposes. However, in another embodiment, more than one excitation signal may be used to excite the area of the sample, in which case only one detection can be used to measure different portions of the emission spectrum. It is envisaged that as the former embodiment may require a spectral shift in the detection bands to measure different portions of the emission spectrum, the latter embodiment may involve a spectral shift in the excitation signals to measure the same different portions of the emission spectrum using a single detection band.

For instance, in some embodiments, first, second and third excitation signals are used to excite the area of the sample with first, second and third spectral contents, each being spectrally shifted from one another. In this specific embodiment, the first, second and third spectral contents can be tuned so that a single detection band can measure the lipid peak band and the first and second lipid band minima. More specifically, the single detection band can measure a first intensity value when the area of the sample is excited using the first excitation signal, the first intensity value being associated to the lipid band peak; the single detection band can measure a second intensity value $I_2$ when the area of the sample is excited using the second excitation signal, the second intensity value $I_2$ being associated to the first lipid band minimum; and the single detection band can measure a third intensity value $I_3$ when the area of the sample is excited using the third excitation signal, the third intensity value $I_3$ being associated to the second lipid band minimum. In such embodiments, the Raman spectroscopic measurement can be performed by estimating a fourth intensity value $I_4$ indicative of optical power of the emission signal at the single detection band based on the second and third intensity values $I_2$ and $I_3$. In this specific embodiment, the estimation can be performed on the basis of a linear regression (e.g., interpolation, extrapolation) using the second and third intensity values $I_2$ and $I_3$ such as to allow the fourth intensity value $I_4$ to be found at the single detection band. Accordingly the fourth intensity value $I_4$ is associated to the lipid band peak minus an average of the first and second lipid band minima. Once the fourth intensity value $I_4$ is determined, the Raman spectroscopy measurement can be performed by comparing the first and fourth intensity values $I_1$ and $I_4$ to one another.

In other embodiments, the system 10 can be alternatively or additionally used determine whether a region of the area 18 of the sample 20 is unhealthy, in which case healthy tissue can be delimited from unhealthy tissue. An example of such determination is described in International Application Publication no. WO2015/154187, which is hereby incorporated by reference.

As can be understood, the controller 16 of FIG. 1 can be provided as a combination of hardware and software components. The hardware components can be implemented in the form of a computing device 1000, an example of which is described with reference to FIG. 10.

Referring to FIG. 10, the computing device 1000 can have a processor 1002, a memory 1004, and I/O interface 1006. Instructions 1008 for performing the Raman measurement(s), and/or the comparison described above, or for determining whether the area of the sample comprises muscular tissue, adipose tissue, healthy tissue and/or unhealthy tissue can be stored on the memory 1004 and accessible by the processor 1002.

The processor 1002 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 1004 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 1006 enables the computing device 1000 to interconnect with one or more input devices, such as the detectors 34 (e.g., hyperspectral or multispectral cameras), position sensor(s), Global Positioning System (GPS) sensor(s), accelerometer(s), humidity sensor(s), keyboard(s), mouse(s) and the like, or with one or more output devices, such as the illumination assembly 12, display(s), user interface(s) and the like.

Each I/O interface 1006 enables the controller 16 of FIG. 1 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

The computing device 1000 described above is meant to be an example only. Other suitable embodiments of the controller 16 of FIG. 1 can also be provided, as it will be apparent to the skilled reader.

Is it envisaged that the controller 16 can have one or more trained engines that are trained using supervised learning. In such supervised learning, each training image in a set of training images may be associated with a label while training. Supervised machine learning engines can be based on Artificial Neural Networks (ANN), Support Vector Machines (SVM), capsule-based networks, Linear Discriminant Analysis (LDA), classification tree, a combination thereof, and any other suitable supervised machine learning engine. However, as can be understood, in some other embodiments, it is intended that the trained engine(s) can be trained using unsupervised where only training images are provided (no desired or truth outputs are given), so as to leave the trained engine(s) find a structure or resemblances in the provided training images. For instance, unsupervised clustering algorithms can be used. Additionally or alternately, the trained engine(s) can involve reinforcement learning where the trained engine(s) interact with example training images and when they reach desired or truth outputs, the trained engine(s) are provided feedback in terms of rewards or punishments. Two exemplary methods for improving classifier performance include boosting and bagging which involve using several classifiers together to "vote" for a final decision. Combination rules can include voting, decision trees, and linear and nonlinear combinations of classifier outputs. These approaches can also provide the ability to control the tradeoff between precision and accuracy through changes in tissue types or thresholds. These methods can lend themselves to extension to large numbers of localized features. In any case, some of these engines may require human interaction during training, or to initiate the engine, however human interaction may not be required while the engine is being carried out, e.g., during analysis of an accessed image. See Nasrabadi, Nasser M. "Pattern recognition and machine learning." Journal of electronic imaging 16.4 (2007): 049901 for further detail concerning such trained engines.

As can be understood, the examples described above and illustrated are intended to be exemplary only. Although the example above involves the use of two excitation signals, other embodiments could involve the use of more than two excitation signals which are slightly spectrally spaced-apart from one another. For instance, three, four, five or more than five excitation signals could be used, which would provide a corresponding number of emission signals. In such embodiments, one or more detection bands can be used to measure the corresponding emission signal(s). While the embodiments presented herein can use a bundle of optical fibres, the methods and systems described herein are not limited to such a bundle of optical fibres. The bundle of optical fibres can thus be omitted. Moreover, in some embodiments described above, the first intensity values are subtracted from the second intensity values. However, in other embodiments, the second intensity values can be subtracted from the first intensity values. Any other suitable arithmetic operation can be performed on the first and second intensity values to compare them to one another. The methods and systems described herein can be used to delimitate two or more molecular constituents such as biological tissue types or other non-biological samples. Examples of spectrally-spaced detection bands can include, but is not limited, a band ranging between 1255-1270 $cm^{-1}$, a band ranging between 1290-1305 $cm^{-1}$, a band ranging between 1440-1455 $cm^{-1}$, and a band ranging between 1650-1665 $cm^{-1}$. The scope is indicated by the appended claims.

What is claimed is:

1. A method for performing a Raman spectroscopy measurement on a sample, said method comprising:
    sequentially illuminating an area of said sample with first and second excitation signals, said first excitation signal being slightly spectrally spaced-apart from said second excitation signal, resulting in said area sequentially emitting first and second emission signals;
    upon receiving said first emission signal, measuring a first intensity value being indicative of optical intensity of said first emission signal within at least a detection band;
    upon receiving said second emission signal, measuring a second intensity value being indicative of optical intensity of said second emission signal within said detection band; and
    performing said Raman spectroscopy measurement by comparing said first intensity value to said second intensity value;
    wherein said sequentially illuminating comprises sequentially illuminating an area of said sample with first, second and third excitation signals, said first, second and third excitation signals being slightly spectrally spaced-apart from one another, resulting in said area sequentially emitting first, second and third emission signals, the method further comprising measuring a third intensity value indicative of optical intensity of said third emission signal within said detection band, said comparing said first intensity value to said second intensity value comprising estimating a fourth intensity value at said detection band based on said first and second intensity values, said performing comprising comparing said fourth intensity value to said third intensity value.

* * * * *